United States Patent [19]

Nakamura et al.

[11] 4,004,582
[45] Jan. 25, 1977

[54] INTRACERVICAL CONTRACEPTIVE DEVICE

[76] Inventors: Robert M. Nakamura, 4633 Brown Deer Lane, Rolling Hills Estates; Val Davajan, 1512 Addison Road, Palos Verdes Estates, both of Calif. 90274

[22] Filed: Oct. 28, 1975

[21] Appl. No.: 626,426

[52] U.S. Cl. .......................... 128/130; 128/260
[51] Int. Cl.² .................................. A61F 5/46
[58] Field of Search ................. 128/127–131, 128/260

[56] References Cited

UNITED STATES PATENTS

| | | | |
|---|---|---|---|
| 2,232,258 | 2/1941 | McCormick et al. | 128/131 |
| 2,422,377 | 6/1947 | Waterbury | 128/127 |
| 2,836,177 | 5/1958 | Sells | 128/127 |
| 3,467,090 | 9/1969 | Zollett | 128/131 |
| 3,690,316 | 9/1972 | Haller | 128/130 |

FOREIGN PATENTS OR APPLICATIONS 945,054  11/1948  France

*Primary Examiner*—Lawrence W. Trapp

[57] ABSTRACT

An intracervical contraceptive device (ICD) is provided with an elongated, circular cylindrical stem having a hollow bore which allows the flow of fluids from the uterus. Two opposed long arms and two opposed short arms are formed at one end of the stem and extend into the uterine cavity to prevent inadvertent expulsion of the device. The long arms flair outwardly in the lateral plane of the uterine cavity while the short arms flair outwardly in a plane parallel to the anterior-posterior plane of the uterine cavity. A barrel-shaped sleeve surrounds the stem and initially conforms to the contour of the walls of the cervical canal. The sleeve is composed of a biodegradable binder material impregnated with a pharmaceutical agent which prevents spermatozoa from performing their fertilization function when the pharmaceutical agent is released into fluids passing over the sleeve. Apertures are provided in the side wall of the stem so that the pharmaceutical agent will also be released into fluids passing through the stem bore.

12 Claims, 7 Drawing Figures

U.S. Patent  Jan. 25, 1977  4,004,582
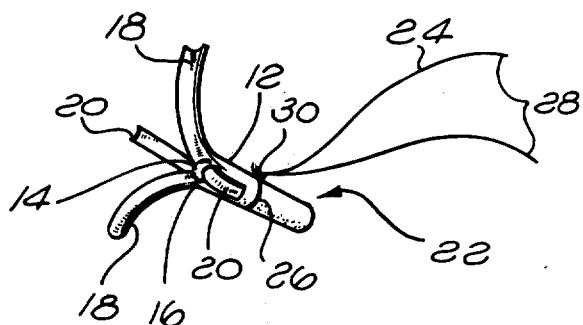
FIG.1.
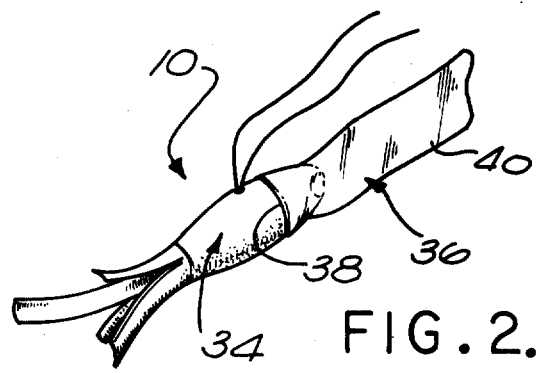
FIG.2.
FIG.3.
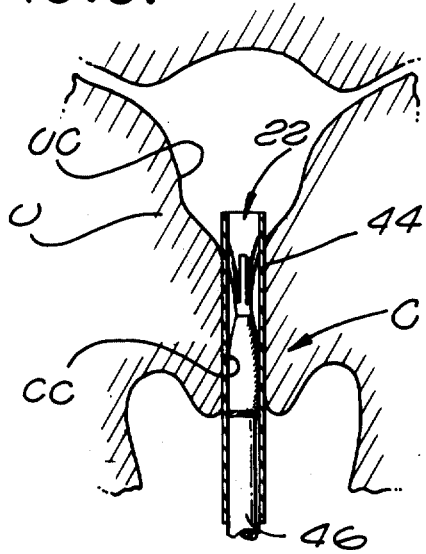
FIG.4.
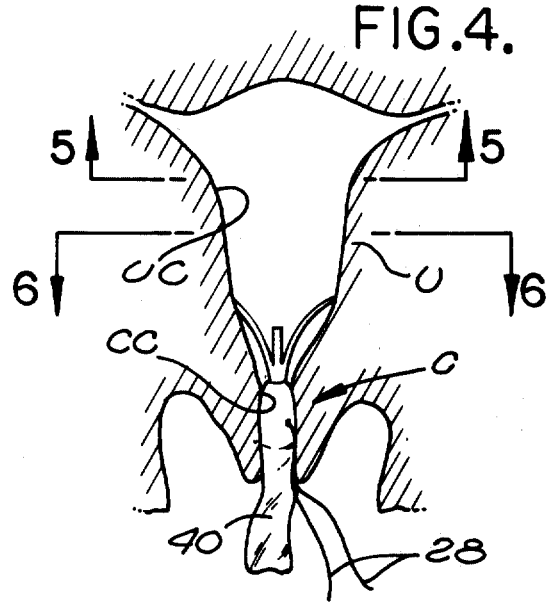
FIG.5.
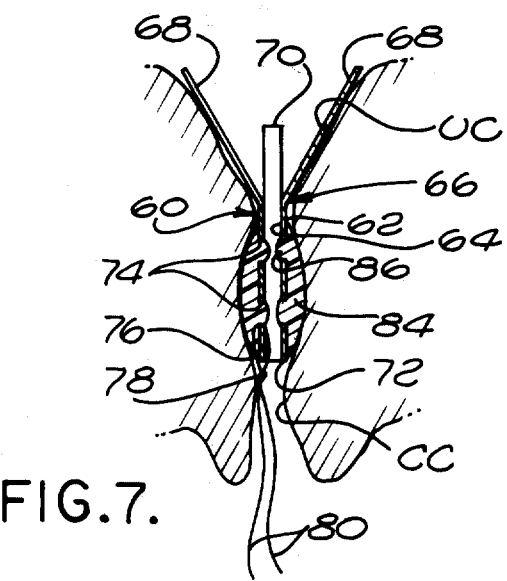
FIG.7.
FIG.6.

INTRACERVICAL CONTRACEPTIVE DEVICE

BACKGROUND OF THE INVENTION

This invention relates to contraceptive devices, and particularly to an intracervical contraceptive device (ICD) which allows the flow of fluids from the uterus while at the same time preventing spermatozoa from performing their fertilization function.

In the field of contraceptive devices, orally administered hormonal "pills" have been found to cause numerous unpleasant secondary side effects, such as circulatory troubles, an increase in weight, dermatological disorders, nausea, and the like. Diaphragms are very inconvenient and have a substantial "failure" rate. Intrauterine devices (IUD) are subject to expulsion (or loss) from the uterus, host intolerance, penetration through uterine tissues, and the like. These IUD side effects naturally result from the IUD's principle of operation which is to irritate the muscle tissue lining the uterus. Furthermore, the IUD is not always effective since it acts at a point after the spermatozoa has had a chance to penetrate into the uterus.

The ICD of this invention provides an apparatus to be inserted into the cervical canal which allows the free flow of fluids from the uterus while at the same time preventing spermatozoa from performing their fertilization function by disrupting spermatozoa transport or causing changes in the spermatozoa prior to entering the uterus. The ICD of this invention does not depend upon irritation for its effectiveness and thus avoids many of the undesirable secondary effects of the IUD. Furthermore, the ICD, once operatively positioned, need not be replaced for an extended period of time. In addition, the ICD of this invention is adapted to be constructed so that the operation of preventing spermatozoa from performing their fertilization function may be accomplished in a variety of ways consistent with the physiological and psychological characteristics of a variety of individuals.

SUMMARY OF THE INVENTION

An intracervical contraceptive device includes a substantially hollow stem adapted to be operatively positioned in a cervical canal and to allow the flow of fluids from the uterus. At least one arm extends outwardly into the uterine cavity from a first end of the stem to prevent inadvertent expulsion of the device. Means are connected to the stem to prevent spermatozoa from performing their fertilization function when the device is operatively positioned. Further means are provided for preventing portions of the device, other than the arm, from entering the uterine cavity after the device is operatively positioned.

In a first embodiment of the invention, the means for preventing entry of the device into the uterine cavity includes a barrel-shaped sleeve surrounding the stem. The end of the stem remote from the uterine cavity terminates within the cervical canal. The means for preventing spermatozoa from performing their fertilization function includes a tight fit between the walls of the cervical canal and the sleeve to prevent the flow of spermatozoa between the sleeve and the cervical canal walls. A one-way valve is connected to the sleeve to allow the flow of fluids from the uterus while preventing the flow of spermatozoa into the uterine cavity through the valve.

In a second embodiment of the invention, apertures are formed in the walls of the stem. The sleeve is partially composed of a pharmaceutical agent which is adapted to be dissolved in fluids passing around the sleeve or through the hollow portion of the stem. The pharmaceutical agent prevents the spermatozoa from performing their fertilization function.

DESCRIPTION OF THE DRAWINGS

This invention will be more readily understood when the following description is taken in conjunction with the drawings, wherein:

FIG. 1 is a perspective view of some of the elements of a first embodiment of the intracervical device of this invention;

FIG. 2 is a perspective view of various other elements assembled to complete the first embodiment of the intracervical device of this invention;

FIG. 3 is a cross-sectional, elevational view illustrating the method of insertion of the intracervical device of the first embodiment in a cervical canal;

FIG. 4 is a partly cross-sectional, perspective view of the first embodiment of this invention operatively positioned in a cervical canal;

FIG. 5 is a cross-sectional plan view taken along the line 5—5 of FIG. 4;

FIG. 6 is a cross-sectional plan view taken along the line 6—6 of FIG. 4; and,

FIG. 7 is a cross-sectional, elevational view of a second embodiment of this invention operatively positioned in a cervical canal.

DETAILED DESCRIPTION

The intracervical contraceptive device (ICD) of this invention includes an elongated, hollow, circular cylindrical stem having four outwardly flaring arms at the first end of the stem. These arms are designed to engage the walls of the uterus adjacent the inner end of the cervical canal (internal os level) to prevent inadvertent expulsion of the ICD. A barrel-shaped sleeve surrounds the stem and substantially conforms to the shape of the walls of the cervical canal. The second end of the stem remote from the flaring arms terminates within the cervical canal to prevent the ICD from being pushed into the uterus. A string is secured to the ICD to assist in removing the ICD.

In a first embodiment of the invention, the sides of the sleeve fit tightly against the walls of the cervical canal to prevent spermatozoa from passing between the sleeve and the cervical canal walls. A one-way valve is secured to the sleeve and surrounds the second end of the stem to allow the passage of fluids from the uterine cavity through the stem and the valve while at the same time preventing the passage of spermatozoa into the uterine cavity through the valve.

In a second embodiment of this invention, a plurality of small apertures are formed on the side wall of the stem and the sleeve is composed of a binder material and a pharmaceutical agent. Portions of the sleeve project into the stem apertures so that the pharmaceutical agent is dissolved in fluids passing through the stem's hollow bore. Similarly, the pharmaceutical agent is dissolved in any fluids passing between the exterior of the sleeve and the walls of the cervical canal. The pharmaceutical, such as a spermatozoidal agent, is designed to prevent spermatozoa from performing their fertilization function.

More specifically, in the first embodiment of the invention shown in FIGS. 1, 2, 4 and 6, the ICD 10 has an elongated, circular cylindrical stem 12 formed of a tube having a hollow bore 14. The stem is composed of a material such as plastic or the like, which will not react with the substances it is anticipated to come in contact with when operatively positioned and which will not injure surrounding tissue. Two pairs of arms 18 and 20 are formed integrally with the first or inner end 16 of the stem and are composed of the same material as the stem. The inner end 16 is designed to be positioned at the inner end of the cervical canal, as will be explained hereinafter. The two long arms 18 flair outwardly into the uterine cavity in the lateral plane of the uterus while the two short arms 20 flair outwardly into the uterine cavity in a plane parallel to the anterior-posterior plane of the uterus, as will be explained hereinafter. The second or lower end of the stem 22 is terminated so that the stem does not extend beyond the outer opening of the cervical canal. In this embodiment of the invention, the length of the stem between its two ends 16 and 22 is about 13 millimeters. A circular groove or notch 26 is formed around the midportion of the stem 12 so that a string 24 tied securely in the groove, as by a knot 30, is sufficiently affixed to the stem to permit the ICD to be removed by pulling on the remote ends 28 of the string.

A sleeve 34, having an external barrel shape is secured around the stem 12 with epoxy glue or the like. The sleeve 34 covers the entire length of the stem 12, from the inner end 16 to the outer end 22, while the string 24 passes through the sleeve. In this embodiment of the invention, the sleeve may be formed in various sizes so that the appropriate dimensions may be selected for various individuals to provide a tight fit between the sleeve and the walls of the cervical canal. This tight fit is sufficient to prevent spermatozoa from passing between the sleeve and the walls of the cervical canal. A one-way valve 36 has a first end 38 secured, by epoxy glue or the like, to the midportion of the sleeve 34. The valve encloses and surrounds the outer end 22 of the stem and has a second end 40 which is adapted to depend outwardly from the cervical canal, as will be explained hereinafter. In this embodiment of the invention, the one-way valve 36 is a Bunsen-type valve which consists of a tube of flexible plastic, rubber, or the like having a flattened end 40. This valve 36 allows fluids to pass from the uterine cavity through the stem and out of the valve end 40 while at the same time preventing spermatozoa and other fluids from entering into the valve from outside the uterus.

The ICD is introduced into the cervix C by any of various well known means. With this embodiment of the invention the arms 18 and 20 are folded together so that the ICD fits into an elongated tubular inserter 44 (FIG. 3) whose upper end is adapted to enter into the cervical canal CC. A plunger 46 slides within the inserter 44 to hold the ICD into position within the cervical canal as the inserter 44 is withdrawn with the plunger 46 maintained in position. After the inserter 44 is withdrawn and the arms 18 and 22 are in engagement with the side walls of the uterus U, the ICD will stay in position as is illustrated in FIG. 4.

When the ICD is operatively positioned, the long arms 18 of the ICD are positioned to lie in the lateral plane 52 of the uterine cavity UC while the short arms 20 lie in a plane parallel to the anterior-posterior plane 54 of the uterine cavity, as is shown in FIGS. 5 and 6.

The arms 18 and 20 are cut to suitable lengths so that the arms 20 will not cause discomfort by protruding too far into the normally closed walls of the uterine cavity while the longer arms 18 are allowed to protrude further into the uterine cavity since the uterine cavity walls perpendicular to the lateral plane 52 are normally remote from one another. In this first embodiment of the invention, the arms 18 are about 10 millimeters long while the arms 20 are about 6 millimeters long.

As is shown in FIGS. 4–6, when the ICD of the first embodiment of this invention is operatively positioned in the cervical canal CC, the sleeve 34 and stem 12 lie entirely within the cervical canal CC. Since the barrel shape of the sleeve matches the distended shape of the cervical canal, the outer walls of the sleeve fit tightly against the walls of a cervical canal. The normally flattened configuration of the cervical canal is thus distended by the sleeve substantially as much as possible as is shown in FIGS. 4 and 6. With the ICD thus operatively positioned, the ends 28 of the string and the end 40 of the valve 36 depend downwardly and outwardly from the cervical canal while the arms 18 and 20 flair outwardly into the uterine cavity UC.

In the first embodiment of the invention, the sleeve is composed of a binder material. One such suitable binder material is a silicon rubber, such as hydrophobic Silastic produced by Dow Chemical Co. While not necessary in this first embodiment, such binder material may be impregnated with a pharmaceutical agent adapted to prevent the spermatozoa from accomplishing their fertilization function. Such binder materials may be either hydrophobic or hydrophilic, depending upon the type of pharmaceutical agent to be employed. One type of pharmaceutical agent which could be employed with silicon rubber, for example, is norethindrone which effects the thickness of the cervical mucus. Another suitable binder material is a biocompatible hydrogel which may be hydrophobic, and thus suitable for impregnation with steroids, or hydrophilic, and thus suitable for impregnation with a spermicidal type pharmaceutical agent. It will be understood that in this first embodiment of the invention, various other types of suitable binder materials may be employed either alone or in conjunction with pharmaceutical agents adapted to be released by the binder material into the fluids passing over the sleeve.

In a second embodiment of the invention, the ICD 60 is composed of an elongated, circular cylindrical stem 62 having a central hollow bore 64. Long arms 68 and short arms 70 are formed integrally with the first or inner end 66 of the stem 62. The second or outer end 72 of the stem terminates within the cervical canal CC. Apertures 74 are formed in the walls of the stem 62 and a string 76 is tied through one of the apertures, as by knot 78, so that the ICD 60 may be extracted from the cervical canal by pulling on the ends 80 of the string 76.

A sleeve 84 is secured around the stem 62 by epoxy glue or the like. In this embodiment of the invention, cap portions 86 of the sleeve 84 extend through the apertures 84 and into the hollow bore 64 of the stem. The ICD 60 is positioned in the cervical canal CC so that the short and long arm 70 and 68 respectively extend into the uterine cavity UC in planes parallel to the anterior-posterior and the lateral planes of the uterine cavity, respectively, as previously explained. When in operative position, the outer end 72 of the stem 62 terminates within the cervical canal CC while the ends 80 of the string 76 depend outwardly from the cervical canal. The ICD 60 thus allows the free flow of fluids through the hollow bore 62, both into and out of the uterine cavity.

In this second embodiment of the invention, the sleeve 84 includes a binder material. A pharmaceutical agent impregnates the binder material, as has been previously described, since the tight fit of the sleeve and the one-way valve are omitted. In addition to the examples of types of binder materials and pharmaceutical agents previously mentioned, the binder material may be a biodegradable material which is either hydrophobic or hydrophilic. Such biodegradable materials may be, for example, polylactate or polyglycolate. Where such a biodegradable binder material is employed, the pharmaceutical agent will be more uniformly released into the fluids passing through the central bore 64 of the tube or between the walls of the cervical canal and the sleeve since the fluids will dissolve both the binder material and the pharmaceutical agent.

Other suitable pharmaceutical agents which may be employed in either the first and second embodiment of this invention include quinine hydrochloride which is spermicial at the pH of the midcycle mucus. Another type of pharmaceutical agent which may be employed is an acrosin inhibitor which changes the characteristics of the spermatozoa so that they are no longer capable of fertilization.

It will be apparent that various modifications and changes may be made in the embodiments of the invention disclosed and described herein, all within the scope of this invention. For example, changes may be made in the configuration of the stem, sleeve or arms as well as in the content of the sleeve constituents.

What is claimed is:

1. An intracervical contraceptive device, comprising:
   a substantially hollow stem adapted to be operatively positioned in a cervical canal and to allow the flow of fluids from the uterus;
   at least one arm connected to a first end of said stem, said arm extending outwardly into the uterine cavity to prevent inadvertent expulsion of said device;
   means connected to said stem adapted to prevent spermatozoa from performing their fertilization function when the device is operatively positioned; and,
   means for preventing portions of the device, other than said arm, from entering the uterine cavity when the device is operatively positioned.

2. An intracervical device as defined in claim 1, wherein said entry preventing means comprises:
   a barrel-shaped sleeve surrounding and connected to said stem, said sleeve substantially conforming to the shape of the cervical canal; and
   the end of said stem remote from the uterine cavity terminating within said cervical canal.

3. An intracervical device as defined in claim 2, wherein said fertilization function preventing means comprises:
   a one-way valve connected to said sleeve, said valve allowing the flow of fluids from the uterus while preventing the flow of spermatozoa into the uterine cavity through the valve; and,
   said sleeve bearing tightly against the walls of the cervical canal to prevent the flow of spermatozoa between said sleeve and cervical canal walls.

4. An intracervical device as defined in claim 2, wherein said fertilization function preventing means comprises:
   at least one aperture formed in a wall of said stem; and,
   said sleeve being at least partially composed of a pharmaceutical agent and being positioned to permit said pharmaceutical agent to be dissolved in fluids passing through the hollow portion of said stem and contacting said sleeve through said aperture.

5. An intracervical device as defined in claim 4, wherein said sleeve is partially composed of a biodegradable substance.

6. An intracervical contraceptive device comprising:
   an elongated, circular cylindrical stem having a hollow bore, said stem being adapted to be positioned in a cervical canal to allow the flow of fluids from the uterus through the stem, said stem having a first end positioned adjacent the uterine cavity and a remote second end positioned within the cervical canal when said device is operatively positioned;
   a first pair of opposed arms flaring outwardly from said first end of said stem, said arms being adapted to extend into the uterine cavity in the lateral plane of the cervical canal to prevent inadvertent expulsion of said device;
   a second pair of opposed arms flaring outwardly from said first end of said stem, said arms being adapted to extend into the uterine cavity in a plane parallel to the anterior-posterior plane of the cervical canal to prevent inadvertent expulsion of said device, said second pair of arms being shorter than said first pair of arms;
   a barrel-shaped sleeve surrounding said stem and bearing tightly against the walls of the cervical canal to prevent the flow of spermatozoa between said sleeve and said cervical canal walls;
   a one-way valve having a first end secured around the periphery of the sleeve and a second end of said stem, said valve allowing the flow of fluids from the uterus through the stem and through the valve while preventing the flow of spermatozoa through the valve into the uterine cavity; and,
   a string having a first end connected to the device and a second end depending from said cervical canal for extracting the device.

7. An intracervical contraceptive device comprising:
   an elongated, circular cylindrical stem having a hollow bore and a plurality of apertures formed in the cylindrical wall of said stem, said stem being adapted to be positioned in a cervical canal to allow the flow of fluids out of and into the uterus through the stem, said stem having a first end positioned adjacent the uterine cavity and a remote second end positioned within the cervical canal when said device is operatively positioned;
   a first pair of opposed arms flaring outwardly from said first end of said stem, said arms being adapted to extend into a uterine cavity in the lateral plane of the cervical canal to prevent inadvertent expulsion of said device;
   a second pair of opposed arms flaring outwardly from said first end of said stem, said arms being adapted to extend into the uterine cavity in a plane parallel to the anterior-posterior plane of the cervical canal to prevent inadvertent expulsion of said device, said second pair of arms being shorter than said first pair of arms;

the barrel-shaped sleeve surrounding said stem, said sleeve substantially conforming to the shape of the cervical canal, said sleeve comprising a binder material and a pharmaceutical agent adapted to be dissolved in fluids passing around said sleeve or through the hollow stem said pharmaceutical agent being adapted to prevent spermatozoa from performing their fertilization function; and, a string having a first end connected to the device and a second end depending from said cervical canal for extracting the device.

8. An intracervical device as defined in claim 7, wherein said binder material is silicon rubber.

9. An intracervical device as defined in claim 7, wherein said binder material is biodegradable.

10. An intracervical device as defined in claim 7, wherein said pharmaceutical agent is a spermicidal agent.

11. An intracervical device as defined in claim 7, wherein said pharmaceutical agent is quinine hydrochloride.

12. An intracervical device as defined in claim 7, wherein said pharmaceutical agent is an acrosin inhibitor.

* * * * *